United States Patent [19]

Neuffer

[11] Patent Number: 5,224,488

[45] Date of Patent: Jul. 6, 1993

[54] BIOPSY NEEDLE WITH EXTENDABLE CUTTING MEANS

[76] Inventor: Francis H. Neuffer, 3917 Kennilworth Rd., Columbia, S.C. 29205

[21] Appl. No.: 938,898

[22] Filed: Aug. 31, 1992

[51] Int. Cl.$^5$ ............................................. A61B 10/00
[52] U.S. Cl. .................................... 128/751; 606/170
[58] Field of Search ........................ 128/749, 751-754, 128/757, 758; 606/47, 167, 170

[56] References Cited

U.S. PATENT DOCUMENTS

| | | | |
|---|---|---|---|
| 1,585,934 | 5/1926 | Muir | 128/754 |
| 2,198,319 | 4/1940 | Silverman | 128/754 |
| 2,655,154 | 10/1953 | Richter | 606/170 |
| 2,730,101 | 1/1956 | Hoffman | 606/170 |
| 2,767,703 | 10/1956 | Nieburgs | 128/2 |
| 3,001,522 | 9/1962 | Silverman | 128/2 |
| 3,055,370 | 9/1962 | McKinney et al. | 128/303 |
| 3,831,585 | 8/1974 | Brondy et al. | 128/2 B |
| 4,517,965 | 5/1985 | Ellison | 128/20 |
| 4,651,753 | 3/1987 | Lifton | 128/751 |
| 5,071,424 | 12/1991 | Reger | 606/170 |
| 5,112,346 | 5/1992 | Hiltebrandt et al. | 606/170 |

FOREIGN PATENT DOCUMENTS

| | | | |
|---|---|---|---|
| 2429462 | 1/1975 | Fed. Rep. of Germany | 606/47 |
| 8905608 | 6/1989 | World Int. Prop. O. | 128/754 |

*Primary Examiner*—Max Hindenburg
*Attorney, Agent, or Firm*—Michael A. Mann

[57] ABSTRACT

A biopsy needle having a strip of material carried within the hollow of the needle that can be extended through a lateral opening in the needle to cut and direct the sample tissue into the needle interior. Pushing on one of the ends of the strip extends it through the lateral opening as the second end is held firm. A twist is formed in the needle so that only one edge extends through the opening and the flat side of the strip guides or directs the severed sample into the needle. Turning a screw in the handle of the needle causes the end of the strip to be pushed and the strip itself to flex through the opening.

17 Claims, 2 Drawing Sheets

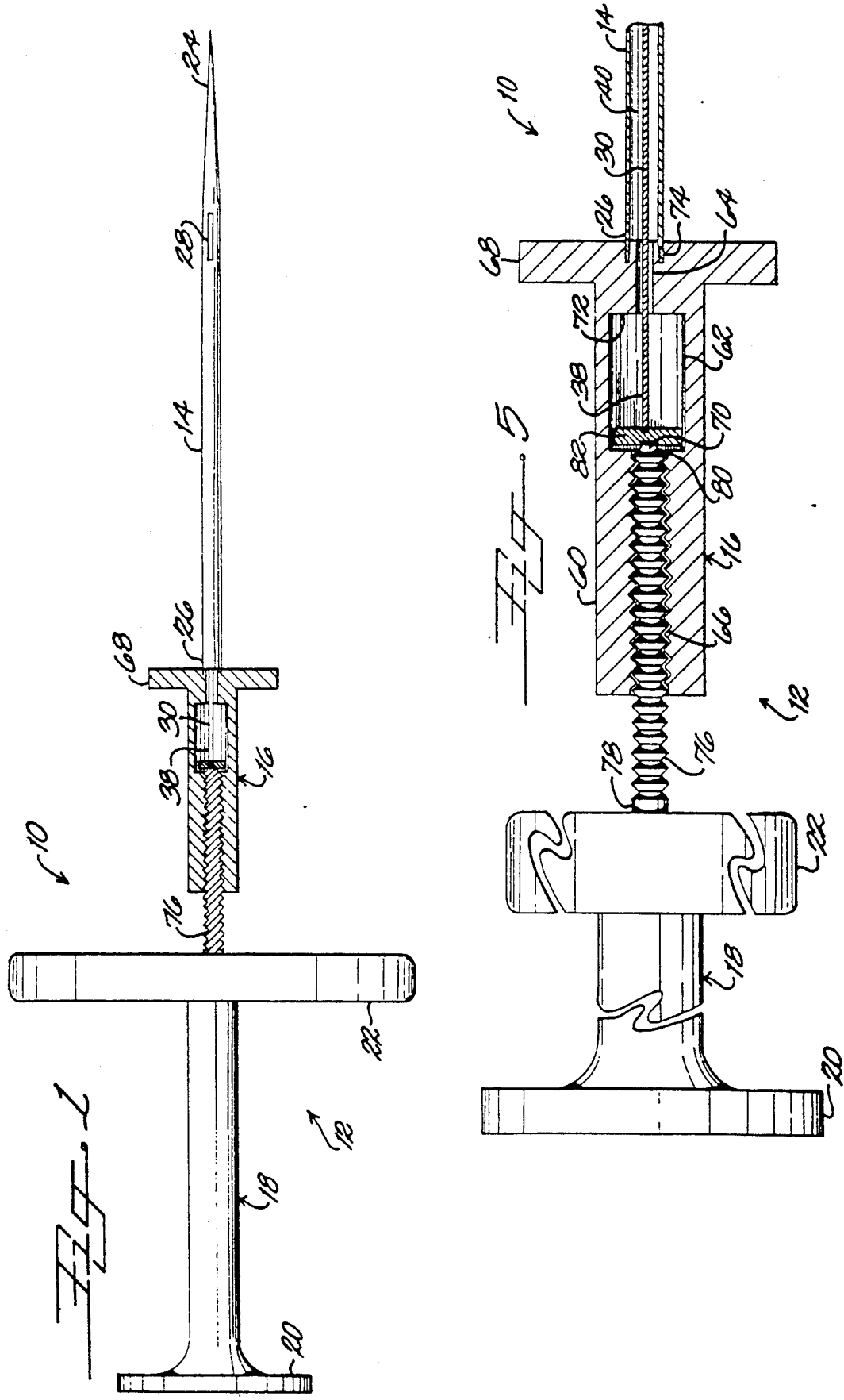

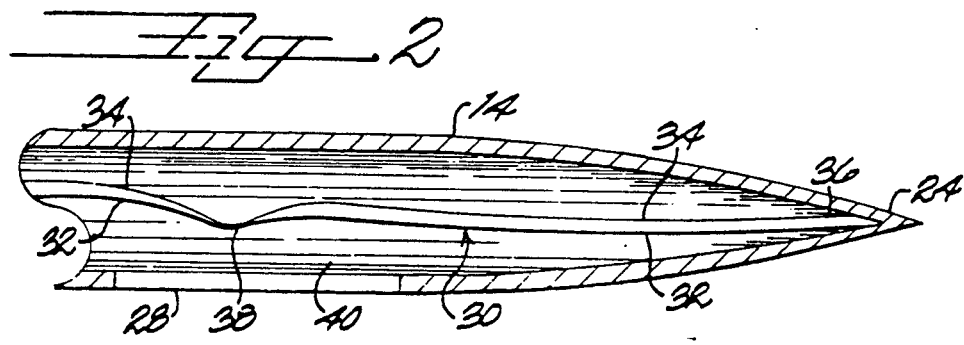
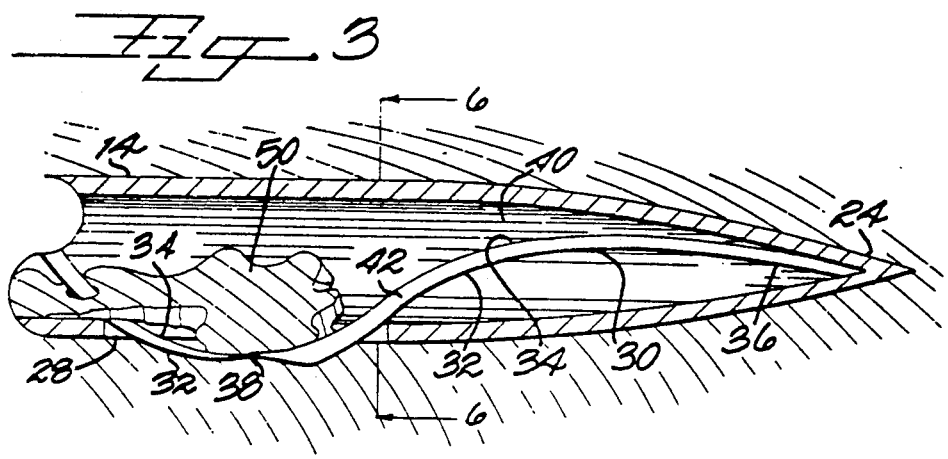
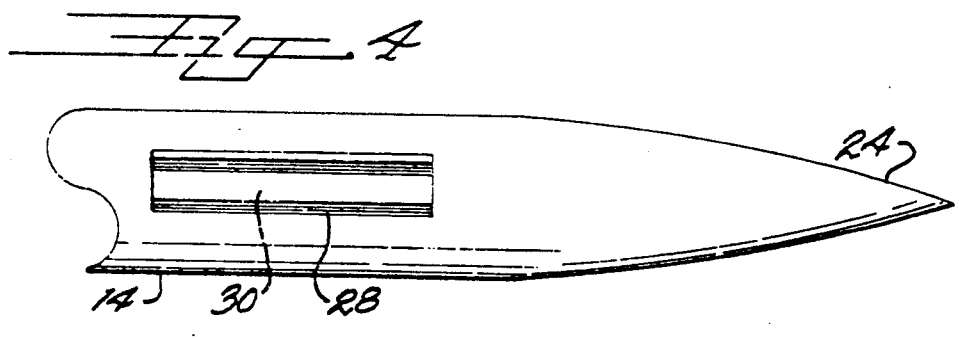
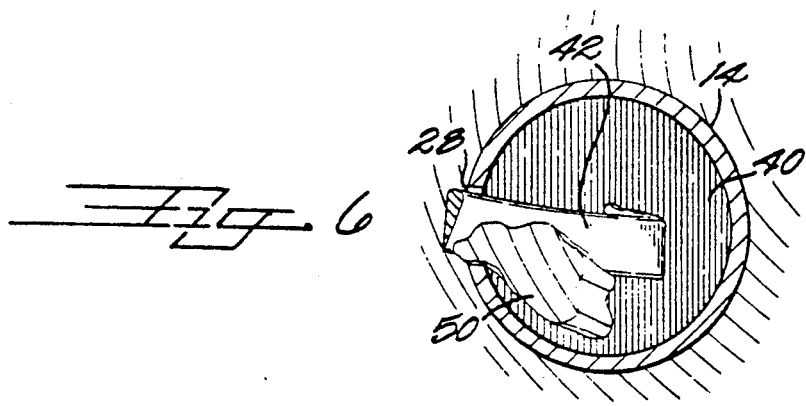

BIOPSY NEEDLE WITH EXTENDABLE CUTTING MEANS

BACKGROUND OF THE INVENTION

1. Field of the Invention

The present invention relates generally to biopsy needles. In particular the present invention relates to needles used for obtaining a sample of tissue from a body for medical evaluation outside the body.

2. Discussion of Background

A biopsy involves removal of a sample of tissue from a body, without significantly affecting the body, for cytological and histological studies. Typically, tissue removal is done with a biopsy needle, a hollow needle with a tissue cutting and securing mechanism. A number of types of such needles are known and readily available.

For example, see U.S. Pat. No. 1,583,934 issued to Muir, U.S. Pat. No. 2,198,319 issued to Silverman, and U.S. Pat. No. 2,767,703 issued to Nieburgs all describe biopsy needles that require some rotation to remove tissue samples.

However, it is an important consideration in biopsy needle design that the amount of tissue removable be sufficient for the types of analysis to be done. Although major improvements have been made in the sensitivity of test procedures and apparatus so that smaller samples have become sufficient for each test, the number of different test procedures and the importance of having the capability for redundant or confirming testing still necessitates having a suitable sample size.

Samples can be obtained in sufficient size by using larger biopsy needles. However, larger needles and sample collecting can be uncomfortable or painful for the patient because they require larger incisions or holes. Larger holes carry an increased risk of iatrogenic complications. If the invaded pathway to the area of the body of interest is reduced in diameter, discomfort and pain are minimized, healing is quicker, scars are less likely to form and the procedures can be done more simply and there is a decrease in the expected mobidity and mortality.

Accordingly, there is a need for a biopsy needle that obtains and secures a sufficiently large sample of tissue with a minimal incision.

SUMMARY OF THE INVENTION

According to its major aspects and broadly stated, the present invention is a biopsy needle for obtaining and securing a sample of tissue from, say, a human or animal. The device comprises a hollow tube having a lateral opening therein. The tube is pointed at one end and attached to a handle at the other end. Inside the tube is a strip of flexible material, preferably also resilient, having a proximal end, toward the handle, and a distal end, toward the point. The distal end is firmly attached to the tube; the proximal end is attached to the handle in such a way that it can be pushed toward the distal end. When pushed, the strip flexes in such a way that a portion of it extends through the lateral opening. The strip has two edges and is twisted so that one of the edges flexes farther from the axis of the tube than the other and will therefore extend through the opening first. Further, the twist enables the strip to be properly oriented, when flexed through the opening, so that the first edge severs the tissue and the strip directs the severed tissue into the interior of the needle as the needle is rotated about the axis. Preferably, the strip is pushed by turning a screw positioned so as to be in operational contact, directly or indirectly, with the proximal end of the strip.

The cooperation of the flexing strip and the lateral opening of the hollow needle is an important feature of the present invention. The strip is oriented to flex through the opening when pushed from one end. Therefore, as the needle is inserted into and withdrawn from the tissue, the strip can be retracted to its interior position thereby reducing the cross-section of the device that penetrates the tissue. When the sample is to be taken, however, the strip is extended through the opening to its extended position to intercept a section of tissue that is to be retrieved.

The twist in the strip is another important feature of the present invention. The twist assures that the strip, when flexed, forms a scoop-like blade, with a first edge oriented to cut into the tissue as the needle is rotated about its axis and the body of the strip oriented to guide or direct the cut tissue into the hollow tube. The twist, therefore, enables a substantial sample to be cut and directed into the interior of the needle without using a large needle.

Another important feature of the present invention is the screw that is used, in a preferred embodiment, to control the flexing of the strip. The screw enables precise control of the flexing and unflexing so that the strip extends just far enough from the tube to get a sample. Stops prevent extreme flexing positions.

The shape of the opening is another feature of the present invention. The opening is preferably a rectangle with its major dimension parallel to the axis of the needle. Most preferably, the opening is a long, thin rectangle, having a major dimension several times its minor dimension. A long, thin rectangle will enable a larger portion of the strip to extend through the opening but allow tissue to enter the tube during positioning of the needle.

Other features and their advantages will be apparent from a careful reading of the Detailed Description of a Preferred Embodiment of the present invention accompanied by the following drawings.

BRIEF DESCRIPTION OF THE DRAWINGS

In the drawings,

FIG. 1 is a partial cross-sectional view of a biopsy needle according to a preferred embodiment of the present invention;

FIG. 2 is a cross-sectional view of a part of the biopsy needle of FIG. 1 with the cutting strip in the retracted position.

FIG. 3 is a side, cross-sectional view of a part of the needle of FIG. 1 with the cutting strip in the extended position;

FIG. 4 is a partial exterior view of the needle of FIG. 1 with the strip of material in the retracted position;

FIG. 5 is a partial side view of the handle of a biopsy needle according to a preferred embodiment of the present invention; and FIG. 6 is an end, cross-sectional view of the needle of FIG. 2 along the line 6—6, with the cutting strip in the extended position.

DETAILED DESCRIPTION OF A PREFERRED EMBODIMENT

The present invention is a biopsy needle. In particular, it is a needle that is inserted into human or animal tissue and that is adapted to extract a small sample of tissue for analysis exterior to the tissue. The needle may be guided into the tissue by radiological imaging to specific locations for removal of the tissue sample for analysis that may include one or more cytologic or histologic tests.

Referring now to FIG. 1, there is shown a partial cross-sectional view of a preferred embodiment of the present invention. Biopsy needle 10 includes handle assembly 12 and elongated hollow tube 14. Handle assembly 12 has hub 16, and gripping portion 18 having grip 20 and flange 22, adapted for holding and manipulation by the practitioner. Hollow tube 14 is preferably pointed at its distal end 24 for ease of insertion into tissue. Tube 14 is attached at its proximal end 26 to hub 16.

Tube 14 has a lateral opening 28 formed therein, near distal end 24. Opening 28 is preferably and generally in the shape of a long, thin rectangle, with the major dimension aligned with the longitudinal axis of tube 14 and the minor dimension perpendicular thereto, as best seen in FIG. 4. The major dimension of opening 28 is preferably a multiple of the minor dimension and the minor dimension is preferably small enough so that tissue does not easily enter tube 14 as distal end 24 is being inserted into the tissue.

Inside hollow tube 14 is cutting strip 30, in the form of a strip of material able to cut tissue, yet preferably flexible and also resilient, such a metal or TEFLON® strip. Cutting strip 30 is flat with two edges, first edge 32 and second edge 34, as shown in FIGS. 2–6. Strip 30 is attached at its distal end 36 to hollow tube 14, toward distal end 24, and, at its proximal end 38, attached to hub 16 in a manner to be described below.

Strip 30 is oriented so that, when proximal end 37 is pushed towards distal end 24 of hollow tube 14, strip 30 flexes and a portion of the flexed strip extends outwards through lateral opening 28 forming a scoop-like blade, as best seen in FIG. 3. Strip 30 can thus be moved between two positions: a retracted position completely within hollow tube 14 and an extended position where a portion of first edge 32 is outside tube 14.

Strip 30 has a twist 38 formed in it along its length where strip 30 extends through opening 28. Twist 38 assures that first edge 32 will flex farther from the centerline or longitudinal axis of hollow tube 14 and through opening 28 first. Twist 38 also assures that first edge 32 and strip 30 itself will be properly oriented to cut or sever a sample of tissue and guide or direct it into interior 40 of hollow tube 14. As indicated in FIGS. 3 and 6, tissue sample 50 slides over flat surface 42 of strip 30 into interior 40 as tube 14 is turned. A 180° turn of needle 10 is approximately one twist of the practitioner's hand. Thus, once needle 10 is in place and strip 30 has been moved to the extended position from the retracted position, a single 180° turn of gripping portion 18 will produce the necessary sample. It will be understood that the size of tube 14 and lateral opening 28 may vary depending on the tissue to be sampled. Preferably, biopsy needle 10, tube 14, and opening 28 are dimensioned so that a turn of needle 10 of approximately 180° will produce a 3 mm × 1 mm sample, sufficient for most analyses.

Twist 38 is preferably a screw-like or propeller-like twist so that first edge 32 extends farther from the longitudinal axis of tube 14 when cutting strip 30 is in its retracted position. Then, as needle 10 is rotated, flat surface 42 of strip 30 between first edge 32 and second edge 34 guides sample 50 with both a longitudinal and a radially inward component to its motion so the resistance of the first part of sample 50 to enter hollow tube 14 does not impede the motion of the remainder of sample 50 into interior 40.

Handle assembly 12, including hub 16 and gripping portion 18, is designed for holding tube 14 and for flexing strip 30. Gripping portion 18 is any type of handle such as is commonly used for syringes. Gripping portion 18 is preferably a standard two-finger-plus-thumb portion having grip 20 and flange 22 for the practitioner to hold when inserting and positioning biopsy needle 10 (FIGS. 1, 6).

Hub 16, shown in cross-section in FIG. 5, includes body 60 with internal cavity 62, bore 64, threaded bore 66, and flange 68. Cavity 62 has first stop 70 at its proximal end and second stop 72 at its distal end. Flange 68 bears a circumferential slot 74 about bore 64, holding therein proximal end 26 of hollow tube 16. Slot 74 is sized to accommodate tube 14, which is affixed therein by any convenient means. Bore 68 communicates with cavity 62 and interior 42 of hollow tube 14.

Threaded bore 66 bears threaded screw 76. Screw 76 is attached at its proximal end 78 to flange 22 of gripping portion 18, and at its distal end 80 to plunger 82. Proximal end 37 of cutting strip 30 is attached to plunger 82. Plunger 82 is contained within cavity 62, and is adapted to slidably rotate within cavity 62 as strip 30 is extended and retracted by turning screw 76 in threaded bore 66.

To take a tissue sample, the practitioner inserts distal end 24 of biopsy needle 10 into the desired location. If convenient, the position of distal end 24 and lateral opening 28 may be guided by radiological imaging to a specific location. After needle 10, and in particular lateral opening 28 are properly positioned, the practitioner holds hub 16 with one hand and rotates gripping portion 18 with the other hand, thereby rotating gripping portion 18 about the longitudinal axis of tube 14 to advance screw 76. As screw 76 advances, plunger 82 pushes proximal end 37 of strip 30 distally, moving twist 38 towards opening 28.

When plunger 82 reaches distal stop 74 of cavity 62, screw 76 cannot be turned further and the practitioner knows that cutting strip 30 is in its extended position. At this point, strip 30 has been extended sufficiently for taking the tissue sample. The whole biopsy needle 10 is then rotated approximately 180°. As needle 10 turns, first edge 32 of strip 30 rotates and cuts a sample of tissue, guiding the cut sample into interior 40 of hollow tube 14. As noted above, a 180° turn of needle 10 will produce the sample.

The practitioner then holds hub 16 and rotates gripping portion 18 in the opposite direction to back screw 76 away from distal stop 72. When plunger 82 reaches proximal stop 70 of cavity 62, strip 30 is in the fully retracted, unflexed position. Needle 10 is withdrawn from the tissue, and the sample is retrieved for analysis.

Preferably, hollow tube 14 is removable from biopsy needle 10 so that the tube with the intact tissue sample can be delivered to an analytical laboratory for analysis of the sample and the remainder of needle 10 reused. It will be evident to one of ordinary skill that this may be accomplished in a number of ways. For example, circumferential slot 74 of hub 16 may be threaded, with proximal end 24 of hollow tube 14 screwed into slot 74. After a sample is taken, tube 14 may be unscrewed and a fresh tube substituted for a new sampling procedure. Alternatively, proximal end 78 of screw 76 may be removably attached to gripping portion 18, such as by press-fitting or screwing into gripping portion 18. Hollow tube 14 may be disposable, as is common with hypodermic syringes and other medical apparatus, or sterilizable and reusable.

Other convenient mechanisms for extending and retracting cutting strip 30 may readily be substituted without departing from the spirit of the present invention. By way of example, instead of screw 76 as described above, a spring and plunger mechanism, biased to hold strip 30 in the retracted position, can be used.

The materials of biopsy needle 10 are preferably sterilizable and such as will not cause undesirable reactions with human tissue. Cutting strip 30 is made of some flexible but resilient material that is able to cut tissue, such as a metal or TEFLON ® strip. Gripping portion 18, hub 16, screw 76, and the other parts of needle 10 may be made of any convenient materials, including but not limited to stainless steel and plastics such as TEFLON ®.

It will be evident that many other changes and modification to the foregoing preferred embodiment can be made without departing from the spirit and scope of the present invention which is to be defined by the appended claims.

What is claimed is:

1. A device for obtaining and securing a sample of tissue, said device comprising:
   a hollow tube having a lateral opening and an axis;
   means carried within said tube for cutting said tissue;
   means for extending at least a portion of said cutting means through said lateral opening so that, when said cutting means is extended and said device is rotated about said axis of said hollow tube, said cutting means cuts said sample and directs said sample into said hollow tube.

2. The device as recited in claim 1, wherein said cutting means further comprises a strip of flexible material.

3. The device as recited in claim 1, wherein said cutting means further comprises a strip of resilient material.

4. The device as recited in claim 1, wherein said cutting means further comprises a strip of flexible material having a first edge and a second edge, said first edge extending farther from said axis toward said opening than said second edge of said strip when said strip is extended by said extending means.

5. The device as recited in claim 1, wherein said cutting means further comprises a strip of material having a proximal end and a distal end, and a first edge and a second edge, said extending means flexing said strip through said lateral opening by moving said proximal end toward said distal end.

6. The device as recited in claim 1, wherein said cutting means further comprises a strip of material having a proximal end and a distal end, and a first edge and a second edge, said distal end being fixed within said hollow tube, and said extending means further comprises means for advancing said proximal end of said strip toward said distal end thereby flexing said strip so that said first edge extends through said opening but not said second edge.

7. The device as recited in claim 1, further comprising a handle and wherein said cutting means further comprises a strip of material having a proximal end and a distal end, said distal end being fixed within said hollow tube, and said extending means further comprises a screw in operational connection with said proximal end of said strip to push said proximal end toward said distal end as said screw is turned thereby pushing said proximal end toward said distal end of said strip so that at least a portion of said strip extends through said opening.

8. A device for obtaining and securing a sample of tissue, said device comprising:
   a handle;
   a hollow tube attached to said handle and having a lateral opening and an axis;
   a strip of material carried within said tube, said strip having a proximal end and distal end, and a first edge and a second edge, said distal end attached to said tube; and
   means carried by said handle for pushing said proximal end of said strip so that said strip flexes toward said lateral opening, said strip having means formed therein for extending said first edge farther from said axis than said second edge, said strip cutting said tissue to form said sample and directing said sample into said hollow tube as said device is rotated, said sample being secured inside said hollow tube.

9. The device as recited in claim 8, wherein said extending means further comprises a twist formed in said strip, said twist formed so that, when said strip is extended through said opening, said first edge extends farther from said axis than said second edge.

10. The device as recited in claim 8, wherein said extending means further comprises a twist formed in said strip, said twist formed so that, when said strip is pushed by said pushing means, said first edge extends farther from said axis than said second edge and said first edge cuts said tissue and said strip directs said tissue into said tube through said opening as said device is turned.

11. The device as recited in claim 8, wherein said pushing means further comprises a screw in operational connection with said proximal end for flexing said strip so that said first edge extends through said opening when said screw is turned.

12. The device as recited in claim 8, wherein said material is resilient.

13. The device as recited in claim 8, wherein said lateral opening is in the shape of a rectangle having a major dimension and a minor dimension, said major dimension being aligned with said axis of said tube.

14. A method for taking a biopsy sample of tissue, said method comprising the steps of:
   inserting a hollow needle having a lateral opening into said tissue;
   flexing a strip of material through said opening, said strip having a first edge and a second edge and a twist formed therein so that said first edge flexes through said opening but not said second edge;
   rotating said needle so that said first edge cuts said tissue sample and said strip directs said sample into said hollow needle;
   drawing said first edge through said opening into said hollow needle; and
   withdrawing said needle from said tissue, said sample secured inside said needle.

15. The method as recited in claim 14, wherein said rotating step further comprises the step of rotating said needle not more than approximately 180°.

16. The method as recited in claim 14, wherein said strip is flexed by pushing said proximal end toward said distal end.

17. The method as recited in claim 14, wherein a screw is in operational connection with said proximal end of said strip and said flexing step further comprises turning said screw so that said screw advances toward said proximal end whereby said proximal end is pushed toward said distal end.

* * * * *